United States Patent
Zeller, III et al.

(10) Patent No.: US 11,780,792 B2
(45) Date of Patent: Oct. 10, 2023

(54) PHOTOCHLORINATION OF PARTIALLY-CHLORINATED CHLOROMETHANES TO CARBON TETRACHLORIDE

(71) Applicant: Occidental Chemical Corporation, Dallas, TX (US)

(72) Inventors: Robert L. Zeller, III, Seabrook, TX (US); Darrell G. Hollis, Conway Springs, KS (US); Keith S. Kramer, Andover, KS (US); Brian Calderwood, Wichita, KS (US); Rodney L. Klausmeyer, Wichita, KS (US); John L. Dawkins, Derby, KS (US)

(73) Assignee: Occidental Chemical Corporation, Dallas, TX (US)

( * ) Notice: Subject to any disclaimer, the term of this patent is extended or adjusted under 35 U.S.C. 154(b) by 135 days.

(21) Appl. No.: 17/417,504

(22) PCT Filed: Jan. 10, 2020

(86) PCT No.: PCT/US2020/013071
§ 371 (c)(1),
(2) Date: Jun. 23, 2021

(87) PCT Pub. No.: WO2020/146722
PCT Pub. Date: Jul. 16, 2020

(65) Prior Publication Data
US 2022/0119326 A1    Apr. 21, 2022

Related U.S. Application Data

(60) Provisional application No. 62/790,934, filed on Jan. 10, 2019.

(51) Int. Cl.
C07C 17/10    (2006.01)
C07C 17/06    (2006.01)

(52) U.S. Cl.
CPC .............. *C07C 17/06* (2013.01); *C07C 17/10* (2013.01)

(58) Field of Classification Search
CPC ...................................... C07C 17/06
See application file for complete search history.

(56) References Cited

U.S. PATENT DOCUMENTS 1,129,165 A    2/1915  Buchner
2,492,417 A    12/1949 Frilette
(Continued)

FOREIGN PATENT DOCUMENTS

CN    103497085 A  *  1/2014
GB    1286939 A   *  8/1972  ............. C07C 17/10
(Continued)

OTHER PUBLICATIONS

CN103497085A, Jan. 2014, pp. 1-23 (Year: 2014).*
(Continued)

*Primary Examiner* — Medhanit W Bahta
(74) *Attorney, Agent, or Firm* — Renner, Kenner; Arthur M. Reginelli (57) ABSTRACT

A method of producing carbon tetrachloride includes providing a chloromethanes stream, combining the chloromethanes stream with chlorine and additional carbon tetrachloride to form a reaction mixture, wherein the reaction mixture includes at least stoichiometric levels of chlorine, introducing electromagnetic radiation to the reaction mixture and subjecting the reaction mixture to suitable reaction conditions to form product carbon tetrachloride, and collecting a product stream including the product carbon tetrachloride.

15 Claims, 4 Drawing Sheets

(56) References Cited

U.S. PATENT DOCUMENTS

| | | | |
|---|---|---|---|
| 2,688,592 | A | 9/1954 | Skeeters et al. |
| 2,945,796 | A | 7/1960 | Saller |
| 3,076,043 | A | 1/1963 | Dehn |
| 3,676,508 | A | 7/1972 | Krekeler et al. |
| 3,954,410 | A | 5/1976 | Pohl et al. |
| 4,101,573 | A | 7/1978 | Gehrmann et al. |
| 4,661,648 | A | 4/1987 | Franklin |
| 6,187,978 | B1 | 2/2001 | Rygas et al. |
| 8,258,353 | B2 | 9/2012 | Kruper, Jr. et al. |
| 8,581,011 | B2 | 11/2013 | Tirtowidjojo et al. |
| 8,907,149 | B2 | 12/2014 | Tirtowidjojo et al. |
| 8,927,792 | B2 | 1/2015 | Tirtowidjojo et al. |
| 9,067,855 | B2 | 6/2015 | Grandbois et al. |
| 9,169,177 | B2 | 10/2015 | Tirtowidjojo et al. |
| 9,199,899 | B2 | 12/2015 | Grandbois et al. |
| 9,233,896 | B2 | 1/2016 | Tirtowidjojo et al. |
| 9,284,239 | B2 | 3/2016 | Grandbois et al. |
| 2014/0221705 | A1 * | 8/2014 | Wang .................... C07C 17/04 570/220 |

FOREIGN PATENT DOCUMENTS

| | | |
|---|---|---|
| WO | 2013096311 A1 | 6/2013 |
| WO | 2017/053528 A1 | 3/2017 |
| WO | 2018/009459 A1 | 1/2018 |

OTHER PUBLICATIONS

International Search Report and Written Opinion for corresponding international application PCT/US2020/013071 dated Apr. 21, 2020 (14 pp).

* cited by examiner

PHOTOCHLORINATION OF PARTIALLY-CHLORINATED CHLOROMETHANES TO CARBON TETRACHLORIDE

This application is a National-Stage application of PCT/US2020/013071 filed on Jan. 10, 2020, which claims the benefit of U.S. Provisional Application Ser. No. 62/790,934 filed on Jan. 10, 2019, which are incorporated herein by reference.

FIELD OF THE INVENTION

Embodiments of the present invention are directed toward chlorination processes that include the photochlorination of partially-chlorinated chloromethanes to carbon tetrachloride.

BACKGROUND OF THE INVENTION

Carbon tetrachloride is a valuable feed stock for the synthesis of many important commercial chemicals. In particular, carbon tetrachloride often serves as a fundamental feed stock for the production of chlorinated propanes, which are used to produce hydrofluoroolefins (HFOs).

While originally formed by reacting chloroform with chlorine, most commercial processes synthesize carbon tetrachloride by chlorinating methane. Industrial methods for the chlorination of partially-chlorinated methanes, such as methyl chloride, methylene chloride, and chloroform to carbon tetrachloride have also been proposed. For example, U.S. Pat. No. 9,169,177 discloses processes for the production of carbon tetrachloride from partially-chlorinated methanes. In order to achieve greater reaction selectivity to carbon tetrachloride, this patent proposes maintaining conversion rates at less than 90%, which produces a product stream including chloroform and carbon tetrachloride with very little production of methyl chloride or methylene chloride. Those chlorinated methanes within the product stream that are not fully chlorinated (e.g. chloroform) are recycled back to the reactor for further chlorination.

In view of the increasing demand for carbon tetrachloride, industrial processes for the efficient synthesis of carbon tetrachloride are desirable.

SUMMARY OF THE INVENTION

One or more embodiments of the present invention provide a method of producing carbon tetrachloride, the method including steps of: providing a chloromethanes stream including chloroform, initial carbon tetrachloride, and at least one of methyl chloride and methylene chloride, wherein the chloromethanes stream includes from about 99.0 to about 100 wt. %, of the chloroform, the initial carbon tetrachloride, and the at least one of methyl chloride and methylene chloride; combining the chloromethanes stream with chlorine and additional carbon tetrachloride to form a reaction mixture, wherein the reaction mixture includes at least stoichiometric levels of chlorine relative to the chloroform and the at least one of methyl chloride and methylene chloride; introducing electromagnetic radiation to the reaction mixture and subjecting the reaction mixture to conditions suitable for reacting the chlorine with the chloroform and the at least one of methyl chloride and methylene chloride to thereby form product carbon tetrachloride; and collecting a product stream after the step of introducing, wherein the product stream includes less than 2,500 ppm (parts per million by weight) of chlorinated hydrocarbons other than carbon tetrachloride.

DETAILED DESCRIPTION OF ILLUSTRATIVE EMBODIMENTS

Embodiments of the invention are based, at least in part, on the discovery of a process for the production of carbon tetrachloride by photochlorination of partially-chlorinated chloromethanes. According to embodiments of the invention, the reaction takes place in a carbon tetrachloride medium that includes relatively high levels of chlorine and relatively low levels of partially-chlorinated chloromethanes. By practicing the methods of this invention, it has unexpectedly been found that industrially useful conversion levels can be achieved with substantial selectivity for carbon tetrachloride. Advantageously, it has been discovered that the formation of hexachloroethane, which results from the dimerization of two trichloromethyl radicals, can be maintained below commercially acceptable levels. As a result, the carbon tetrachloride product produced according to embodiments of the invention can be directly employed, as a crude product stream, in subsequent synthetic processes, such as the Kharasch reactions, without the need for costly purification to remove undesired heavy chlorinated organics.

Process Overview

Figure 1:
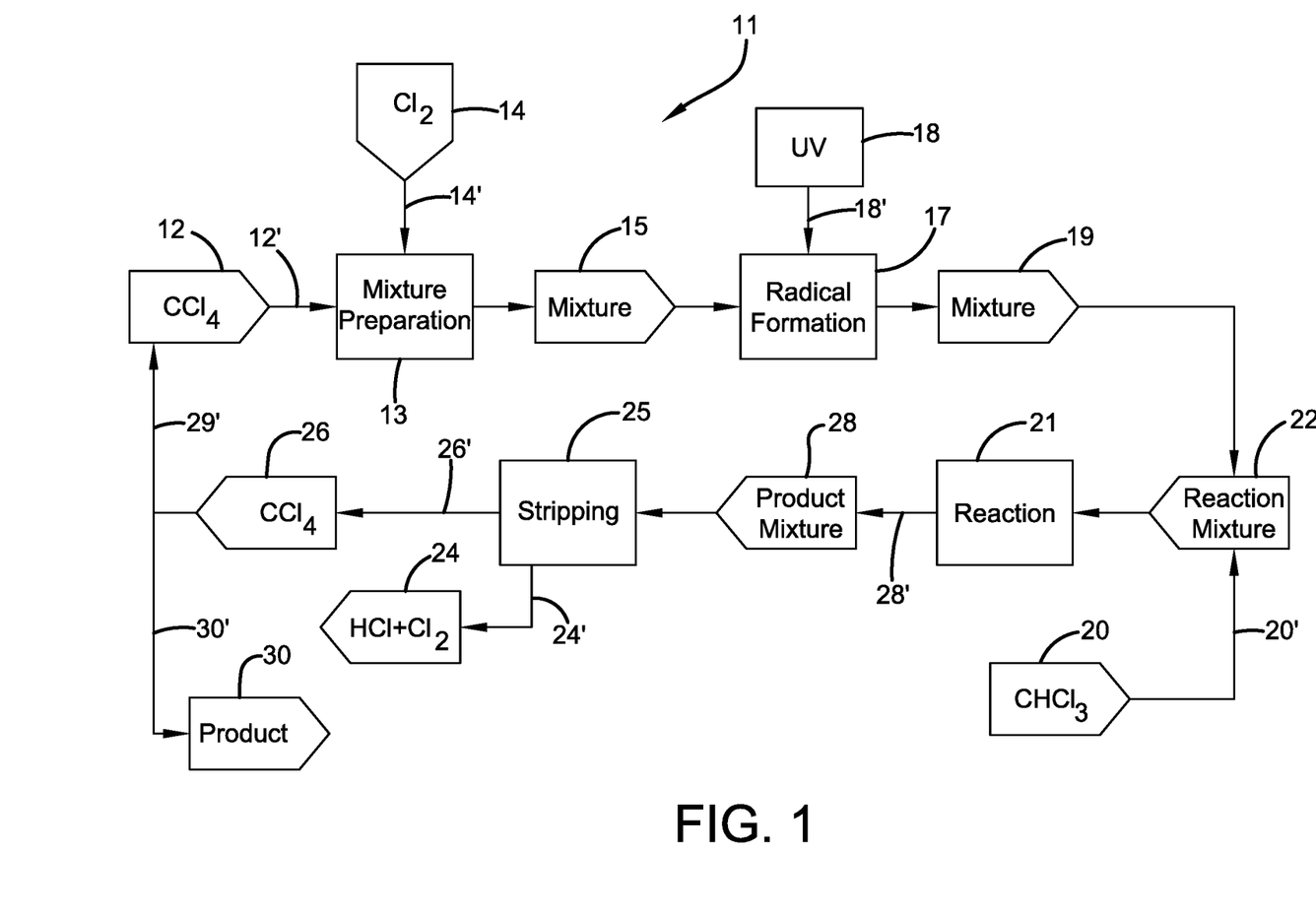
FIG. 1 is a flow chart representation of a process according to one or more embodiments of the present invention.

An overview of one or more embodiments of the present invention can be described with reference to FIG. 1, which shows a chlorination method 11. A carbon tetrachloride feed stream 12' and a chlorine gas feed stream 14' provide carbon tetrachloride 12 and chlorine gas 14 to introduction step 13 where carbon tetrachloride 12 and chlorine gas 14 are combined to thereby form a mixture 15 of carbon tetrachloride 12 and chlorine gas 14, which may also be referred to as initial mixture 15. Initial mixture 15 of carbon tetrachloride and chlorine gas is then subjected to electromagnetic radiation 18' from an electromagnetic radiation source 18 in a free radical forming step 17. Free radical forming step 17 forms a mixture 19 of chlorine gas, carbon tetrachloride, and chlorine free radicals, which may also be referred to as free radical mixture 19. The chlorine free radicals may also be referred to as chloride radicals.

A chloromethanes stream 20', which may also be referred to as an organic-compound containing feed stream 20' or a chloroform feed stream 20', introduces chloromethanes 20, such as chloroform 20, to free radical mixture 19 to form reaction mixture 22. As generally known in the art, the term chloromethanes encompasses methyl chloride, methylene chloride, chloroform, carbon tetrachloride. The methyl chloride, methylene chloride, and chloroform may be further defined as partially-chlorinated chloromethanes or partially-chlorinated methanes. To the extent that chloroform is one of the targeted chloromethanes, aspects of the invention may be described with reference to chloroform and the skilled person will recognize that other chloromethanes may be applicable to those aspects of the invention.

A reaction step 21 takes place that converts partially-chlorinated chloromethanes, such as chloroform, within chloromethanes 20 to carbon tetrachloride, which is the desired product, and produces hydrochloric acid 24, which is a reaction byproduct. Carbon tetrachloride, chlorine, and hydrochloric acid are contained within product mixture 28 that may be identified as an intermediate product stream 28', or crude product stream 28', from reaction step 21. Crude product stream 28' may then be subjected to one or more additional processing steps 25, such as a stripping step 25, which may include, for example, gas stripping, which may utilize an inert gas, which concentrates the carbon tetrachloride 26, via purified stream 26', by removing at least a portion of the chlorine and hydrochloric acid 24, via gas stream 24'. In one or more embodiments, at least a portion of chloromethanes stream 20' may be utilized in stripping step 25 as a scrubbing medium to remove chlorine and/or hydrochloric acid 24 from crude product stream 28'.

In one or more embodiments, at least a portion of the purified carbon tetrachloride 26 may be recycled back to reaction step 21 via recycle stream 29'. At least a portion of purified carbon tetrachloride 26 may otherwise be recovered as product 30 via purified product stream 30'. As indicated above, purified stream 26' may advantageously be directly used as a reactant stream in subsequent chemical synthesis without the need for distillation processes that may otherwise be required to remove organic species such as heavy chlorinated organic compounds that are often a byproduct in the manufacture of chlorinated organics. With that said, it may nonetheless be desirable to further purify the product stream for particular uses. Accordingly, certain embodiments of this invention may include distillation processes to further purify stream 26'. In one or more embodiments, the purification and/or distillation processes remove components other than carbon tetrachloride from stream 26'. In one or more embodiments, the purification and/or distillation processes to further purify stream 26' include removing an amount of partially-chlorinated chloromethanes from stream 26'. The recovered partially-chlorinated chloromethanes may be utilized as a recycle stream back to the process, such as part of chloromethanes stream 20'. In one or more embodiments, the purification and/or distillation processes to further purify stream 26' include removing an amount of chlorine from stream 26'. The recovered chlorine may be utilized as a recycle stream back to the process, such as part of chlorine gas feed stream 14'.

Figure 2:
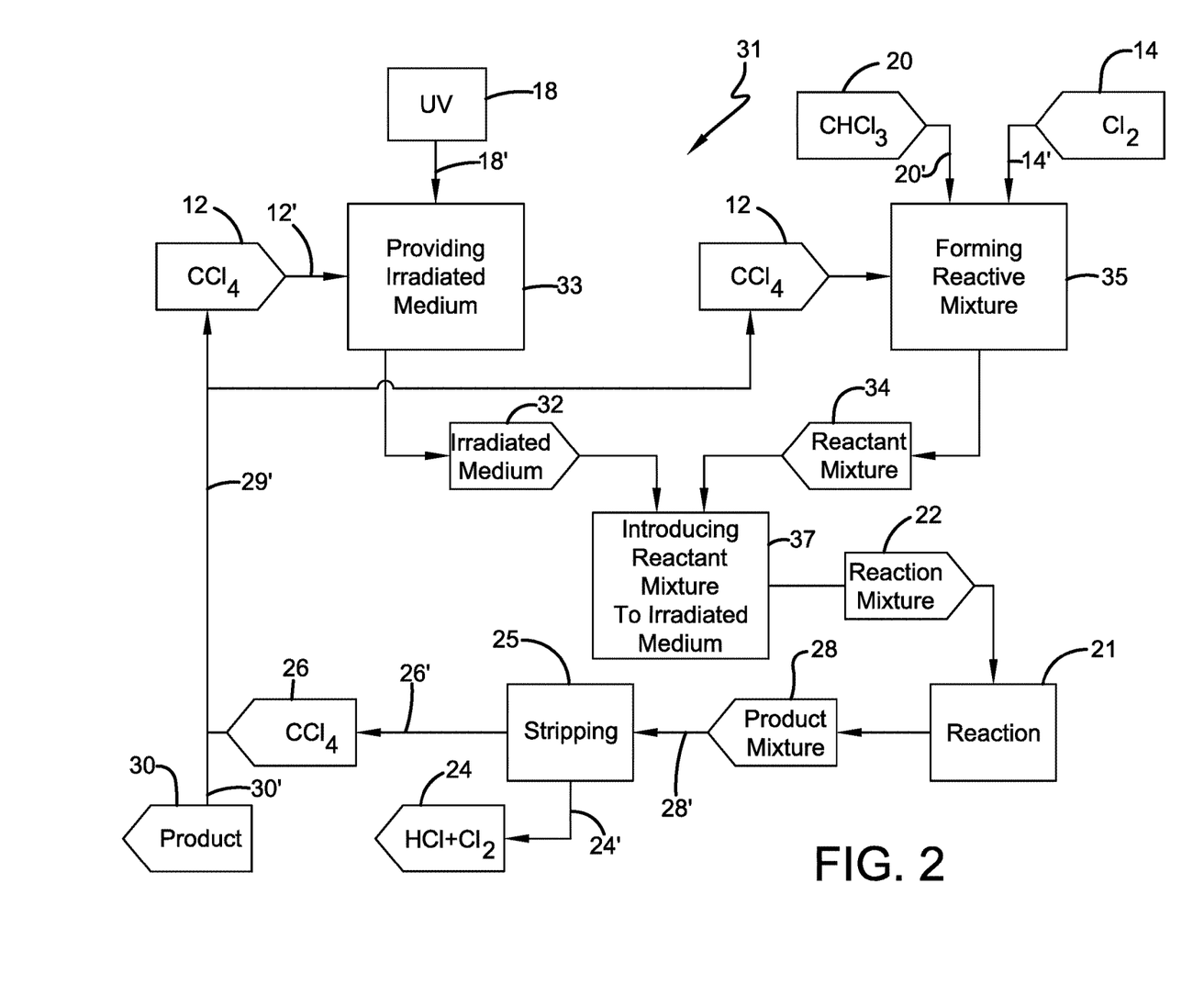
FIG. 2 is a flow chart representation of a process according to one or more embodiments of the present invention.

An alternate process scheme can be described with reference to FIG. 2, which shows chlorination method 31. Carbon tetrachloride 12 from feed stream 12' is combined with electromagnetic radiation 18' from radiation source 18 to provide an irradiated medium 32 within introducing step 33. Chloromethanes 20, such as chloroform 20, from feed stream 20' are combined with chlorine 14 from feed stream 14' to form reactant mixture 34 within combining step 35. Carbon tetrachloride may optionally be combined with chloromethanes 20, such as chloroform 20, and chlorine 14 within this step.

Irradiated medium 32, which may be continually subjected to the electromagnetic radiation, and reactant mixture 34 are introduced in step 37 to form reaction mixture 22 to give rise to reaction step 21, which converts chloroform, methyl chloride, and methylene chloride 20 to carbon tetrachloride (i.e. the chloroform is chlorinated) and produces hydrochloric acid as a reaction byproduct. Carbon tetrachloride and hydrochloric acid are contained within product mixture 28 that may be identified as an intermediate product stream 28', or crude product stream 28', from reaction step 21. Crude product stream 28' may then be subjected to one or more additional processing steps 25, such as a stripping step 25, which may include, for example, a gas stripping, which concentrates the carbon tetrachloride 26, via purified stream 26', by removing at least a portion of the chlorine and hydrochloric acid 24, via gas stream 24'.

In one or more embodiments, at least a portion of the carbon tetrachloride 26 may be recycled back to initial step 33 and/or step 35 via recycle stream 29'. At least a portion of purified carbon tetrachloride 26 may otherwise be recovered as product 30 via purified product stream 30'. As indicated above with respect to FIG. 1, additional purifications, such as distillations, may be avoided. Yet, in other embodiments, further purifications including distillations may be desired.

System for Performing Photochlorination

A system for performing the methods of the invention can be described with reference to FIG. 3, which shows a system 51 for performing a chlorination method. System 51 includes reaction vessel 53, which includes inlet 57, vent 61, lamp 63, agitation element 65, and product outlet 67.

According to exemplary embodiments, chloromethanes 54, such as chloroform 54, via chloromethanes feed stream 54', which may also be referred to as chloroform feed stream 54', is combined with carbon tetrachloride via, for example, recycle stream 75' to form a reactant pre-mixture. Chlorine 52, via feed stream 52', is then combined (via, for example, an in-line sparger) with the reactant pre-mixture, which contains chloromethanes, such as chloroform and carbon tetrachloride, to form a reactant mixture within stream 77'. As mentioned elsewhere herein, iron and other impurities may be removed from chlorine 52 by way of an impurity removing apparatus or technique, such as a filter. As shown in FIG. 3, the chloroform and carbon tetrachloride can be mixed or otherwise agitated within a mixing device, such as an in-line mixer 55, prior to introduction of the chlorine. In other embodiments, which are not shown, the mixture including the chlorine, chloroform, and carbon tetrachloride, which is contained in stream 77, can likewise be agitated, such as in an in-line mixer, prior to introduction into reactor 53. In these embodiments, the chlorine and chloromethanes may be mixed in the absence of light, which may be referred to as dark zone mixing. Feed stream 77' is then introduced to reactor 53 via inlet 57.

As explained above, electromagnetic radiation from lamp 63 causes a chlorination reaction whereby chloroform is converted to carbon tetrachloride. The resultant carbon tetrachloride product is removed from reactor 53 via outlet 67 as product stream 66', which may also be referred to as crude product stream 66'. Product stream 66' may also include one or more of chloroform, chlorine, and hydrogen chloride, as well as other by-products at relatively low levels. Gaseous byproducts, such as hydrogen chloride and chlorine, can be removed from reactor 53 via vent 61 to form stream 79'. This stream may be neutralized for disposal or further separated to isolate chlorine and hydrochloric acid, which may then be used in other synthetic chemical processes and/or recycled back to this process 51.

Crude product stream 66' can be routed to tank 69, which may include a degassing tank, where crude product stream 66' can be concentrated by removal of light constituents such as chlorine and hydrogen chloride via gas stream 69', which can be combined with stream 79'. Through, for example, pump 71, crude product stream 66', which includes concentrated carbon tetrachloride, can be routed through recirculation loop 71', back to reactor 53 via carbon tetrachloride feed stream 75'. Alternatively, the concentrated crude product stream can be routed out of the system for storage and further use via carbon tetrachloride product stream 73'.

In one or more embodiments, carbon tetrachloride product stream 73' can be subjected to additional electromagnetic radiation (as described herein relative to lamp 63), supplied from, for example, a polishing UV reactor or the like, to thereby photochlorinate any residual chloroform and/or other residual organics within the product stream. In one or more embodiments, additional chlorine can be added to the product stream treated in this downstream polishing reactor. In certain embodiments, the polishing reactor may be a tubular reactor. In other embodiments, the polishing reactor may be a CSTR or well mixed reactor. In one or more embodiments, the residual chloroform may instead be collected and recycled back to process 51.

It should be appreciated that according to certain embodiments of the invention, recirculation loop 71' is optional inasmuch as crude product stream 66' can be directly routed to other processes (i.e. stream 66' can be directly routed to 73'). In these embodiments, however, alternate sources of carbon tetrachloride must be used for the reaction medium.

It should therefore be appreciated that the process (and system) of the present invention can be operated as a continuous process wherein reactants are continuously fed to a reactor and product is continuously removed from the reactor. Moreover, the process requirements for carbon tetrachloride can be satisfied from the product stream deriving from the system (e.g. carbon tetrachloride product stream 66' can be recycled back to reactor 53 via input stream 75'). In one or more embodiments, following initial start-up of the system, where external sources of carbon tetrachloride are required (e.g. carbon tetrachloride 12), the process of the invention can receive greater than 90%, in other embodiments greater than 95%, and in other embodiments greater than 99% of the carbon tetrachloride requirements for the operation of the system from carbon tetrachloride recycled from the system (e.g. recycled through loop 71').

It should also be appreciated that various modifications can be made to system 51 without departing from the present invention. For example, chlorine 52 and chloroform 54 can be directly injected into reactor 53 via respective feed streams without the need to premix chlorine 52 and chloroform 54 prior to introduction into reaction vessel 53. In particular embodiments, chloroform feed stream 54' can be introduced below the liquid level within the reactor (e.g. via a dip tube). In these or other embodiments, chlorine feed stream 52' can likewise be introduced below the liquid level via, for example, a sparger. In one or more embodiments, the separate and distinct feed streams can be first combined with carbon tetrachloride and then directly introduced into reactor 53. Also, reactor 53 can be configured to provide for flow of material from the bottom to the top of the reactor, as generally shown in FIG. 3, or the flow of the material can be reversed such that inputs are received at the top of the reactor and the product is removed from the bottom of the reactor.

In one or more embodiments, inlet 57 may include a dispersing device such as a sparger or dip tube, and vessel 53 may include multiple inlets (not shown).

Figure 3:
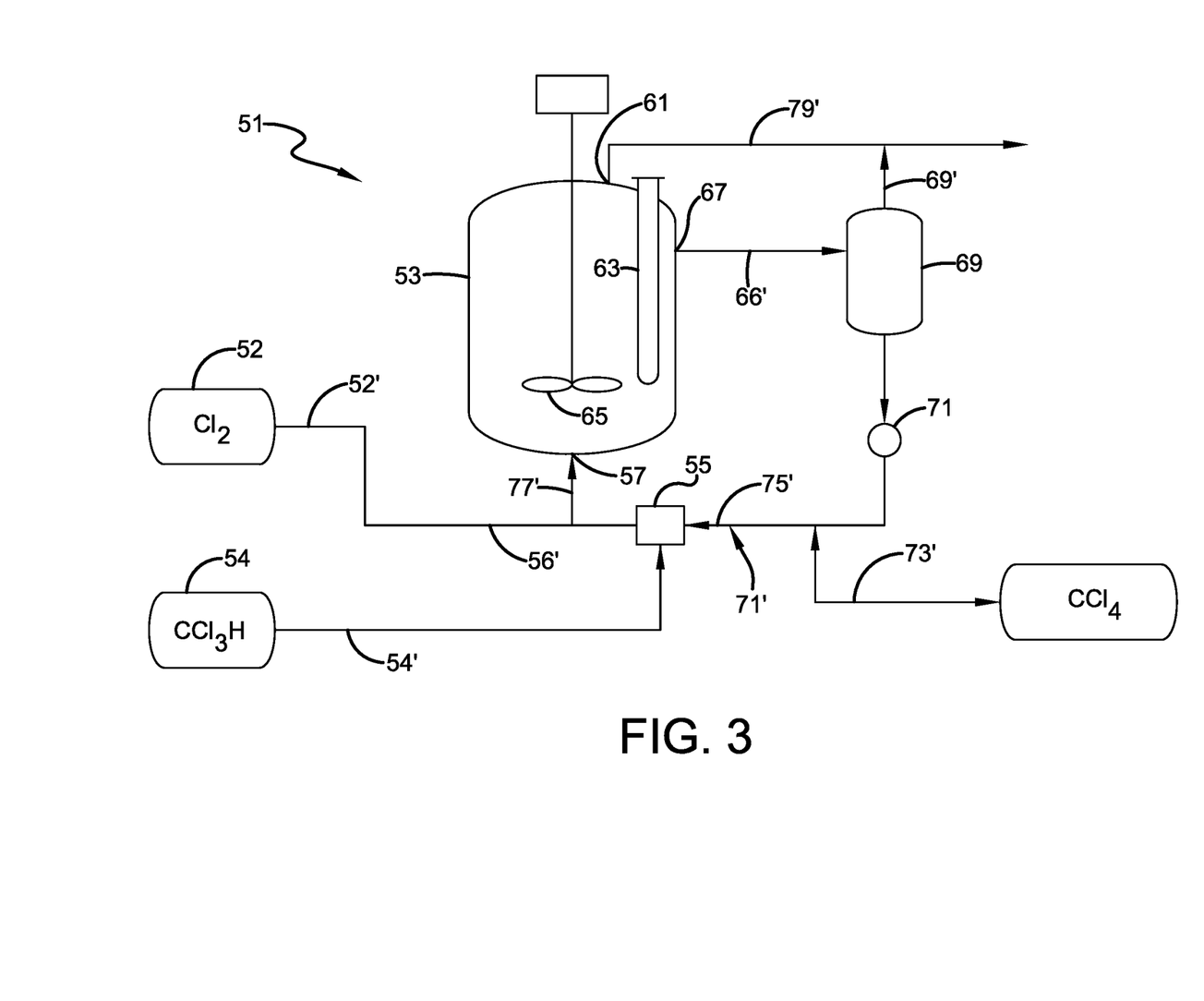
FIG. 3 is a schematic representation of a system for conducting a process according to embodiments of the present invention.

In one or more embodiments, vessel 53 may include a single lamp, as shown in FIG. 3, or it may include multiple lamps. In one or more embodiments, lamp 63 may include ultraviolet lamps, lasers, and light-emitting diodes (LEDs). In one or more embodiments, the lamps include mercury vapor arc lamps such as Hanovia lamps. In one or more embodiments, the lamp(s) (e.g. lamp 63) may be at least partially immersed within the reactor or reaction medium contained within vessel 53 or they may be fully immersed in the reaction medium. In other embodiments, not shown, the lamps, may be external to the interior of the reactor but nonetheless situated to emit the desired electromagnetic radiation into the reactor medium.

In some embodiments, lamp 63 or the assembly housing lamp 63, may be equipped with a physical wiper system and/or a chemical wiping system to reduce scale formation that is believed to be caused by iron compounds that are derived from iron impurities introduced in one of the reactant streams. These impurities may lead to scale forming on lamp 63, particularly an outer surface thereof that is exposed to the process. In one or more embodiments, the recirculation loop may include a filter and/or another impurities removal technique in order to collect the impurities, such as scale or iron compounds, that may be in the outlet of the reactor.

Also, reaction vessel 53 may be equipped with a temperature regulating system such as a heating/cooling jacket. In one or more embodiments, agitation element 65 may include a single mechanical agitator, such as shown in FIG. 3, or multiple agitation devices may be employed. Various mixing configurations can be used including top and bottom mounted mixers. In one more embodiments, the one or more mechanical agitators may be characterized by mixing power. In one more embodiments, mixing power of the one or more mechanical agitators may be from 0.02 kilowatts per cubic meter to 2.0 kilowatts per cubic meter, in other embodiments, from 0.04 kilowatts per cubic meter to 1.0 kilowatts per cubic meter, and in other embodiments, from 0.1 kilowatts per cubic meter to 0.4 kilowatts per cubic meter.

In one or more embodiments, the reaction mixture (e.g. mixture 22 or the contents of reactor 53) may be devoid of the use of a mechanical agitator. In these or other embodiments, some minimal amount of agitation, but a suitable amount of agitation to accomplish the desired reaction, may occur based simply on the introduction of the one or more feed streams and/or one or more recirculation streams and/or product formation in the form of gaseous products, such as HCl.

In one or more embodiments, reactor 58 is configured to include a dark zone, which is an area within the reactor that is not subjected to appreciable levels of electromagnetic radiation that gives rise to the desired photochlorination reaction described herein. The dark zone may advantageously provide time and space for the input stream 77' to become diluted and well mixed within the greater volume of carbon tetrachloride contained within reactor 53 prior to the chlorine becoming radicalized and/or the chloride radicals reacting with the chloroform in the presence of appropriate electromagnetic radiation. As the skilled person will appreciate, the dark zone can be created by employing several mechanisms. For example, a physical obstruction can be placed within the reactor to thereby shield an area from the electromagnetic radiation emitted from lamp 63. Alternatively, or in combination with a physical obstruction, a dark zone can be formed by providing adequate distance between lamp 63 and the desired location of the dark zone. In one or more embodiments, inlet 57 may be desirably located within or adjacent to the dark zone.

It should be appreciated that at start up, reactor 53 may be initially charged with carbon tetrachloride to form an initial medium in which the reaction takes place. In one or more embodiments, the reactor is devoid or substantially devoid of chloroform at the beginning of the reaction so as to avoid having excess chloroform relative to chlorine at any point in the reaction. Once the reaction is underway, the appropriate balance of chlorine and chloromethanes, such as chloroform, and hence carbon tetrachloride as well, within reactor 53, which balance will be described herein below, can be maintained by regulating the chlorine, chloroform, and optionally carbon tetrachloride inputs into reactor 53.

While this system has been described with reference to specific embodiments of the invention, the skilled person can adapt the system, without undue calculation or experimentation, to accommodate other processes described herein.

Processing Chlorine Feed Stream

In one or more embodiments, the chlorine gas feed stream may be subjected to purification techniques prior to introducing the chlorine gas feed stream (e.g. to combining step 35). One or more of these techniques may take place in a chlorine purification unit. In one or more embodiments, this may include sparging the chlorine gas feed stream with nitrogen or other inert media, such as argon, prior to introduction of the chlorine gas feed stream. In these or other embodiments, the chlorine gas feed stream, or a prior liquefied chlorine stream, may be cooled and/or vented in order to reduce the solubility of oxygen and other components in the stream. These solubility-reduced components may thereby be vented from the chlorine gas feed stream, or the prior liquefied chlorine stream. In one or more embodiments, the chlorine gas feed stream may be distilled. This distillation may include removing lighter components (e.g. oxygen) and/or heavier components (e.g. iron, bromine, and bromyl chloride).

In one or more embodiments, a purification technique for the chlorine gas feed stream includes removing iron, such as by filtering, from the chlorine gas feed stream prior to introducing the chlorine gas feed stream. Other exemplary purification techniques for the chlorine gas feed stream, such as for removing iron, include sequestration, cation exchange, and oxidation.

Oxygen Removal Step

Components of the process (e.g. reactor and associated piping) may be purged of oxygen as a part of start-up operations, which may include a nitrogen sweep, in order to reduce or eliminate oxygen from the operational process. One or more particular aspects of an oxygen purge may be generally known to the skilled person.

Characteristics of Carbon Tetrachloride Feed Stream

In one or more embodiments, carbon tetrachloride feed stream (e.g. 12', 75') is substantially carbon tetrachloride, which refers to a feed stream that does not include appreciable amounts of constituents other than carbon tetrachloride. In one or more embodiments, carbon tetrachloride feed stream (e.g. 12', 75') consists essentially of carbon tetrachloride, which refers to a composition that is free of other constituents that would otherwise materially impact the basic and novel characteristics of embodiments of the invention. In one or more embodiments, carbon tetrachloride feed stream (e.g. 12', 75') consists of carbon tetrachloride. In one or more embodiments, the carbon tetrachloride is technical-grade carbon tetrachloride. In one or more embodiments, carbon tetrachloride feed stream 12', 75' includes from about 99.9 to about 100 wt %, carbon tetrachloride. In one or more embodiments, carbon tetrachloride feed stream (e.g. 12', 75') includes less than 7000 ppm, in other embodiments less than 6000 ppm, in other embodiments less than 5500 ppm, in other embodiments less than 5000 ppm, in other embodiments less than 2500 ppm, in other embodiments less than 1000 ppm, in other embodiments less than 750 ppm, in other embodiments less than 500 ppm, and in other embodiments less than 100 ppm of chlorinated organic constituents other than carbon tetrachloride.

Characteristics of Chlorine Feed Stream

In one or more embodiments, chlorine feed stream (e.g. 14', 52') is substantially chlorine gas, which refers to a feed stream that does not include appreciable amounts of constituents other than chlorine gas. In one or more embodiments, chlorine gas feed stream (e.g. 14', 52') consists essentially of chlorine gas, which refers to a composition that is free of other constituents that would otherwise materially impact the basic and novel characteristics of embodiments of the invention. In one or more embodiments, chlorine gas feed stream (e.g. 14', 52') consists of chlorine gas. In one or more embodiments, chlorine feed stream (e.g. 14', 52') includes from about 99.5 to about 100 vol %, chlorine. In one or more embodiments, chlorine feed stream (e.g. 14', 54') includes less than 5000 ppm, in other embodiments less than 1000 ppm, in other embodiments less than 750 ppm, in other embodiments less than 500 ppm, in other embodiments less than 250 ppm, in other embodiments less than 100 ppm, in other embodiments less than 50 ppm, and in other embodiments less than 25 ppm of constituents other than chlorine.

In one or more embodiments, chlorine gas feed stream (e.g. 14', 52') is substantially devoid of oxygen, which refers to a feed stream that does not include appreciable amounts of oxygen. In one or more embodiments, chlorine feed stream (e.g. 14', 52') includes less than 2500 ppm, in other embodiments less than 1000 ppm, in other embodiments less than 750 ppm, in other embodiments less than 500 ppm, in other embodiments less than 250 ppm, in other embodiments 100 ppm, in other embodiments less than 50 ppm, in other embodiments less than 30 ppm, in other embodiments less than 20 ppm, and in other embodiments less than 15 ppm of oxygen. In general, lower amounts of oxygen in chlorine gas feed stream allow higher chlorination reaction rates.

In one or more embodiments, chlorine gas feed stream (e.g. 14', 52') is substantially devoid of iron, which refers to a feed stream that does not include appreciable amounts of iron. In one or more embodiments, chlorine feed stream (e.g. 14', 52') includes less than 3 ppm, in other embodiments less than 2 ppm, in other embodiments less than 1.5 ppm, in other embodiments less than 1 ppm, and in other embodiments less than 0.5 ppm of iron.

Characteristics of Chloromethanes Stream

In one or more embodiments, chloromethanes stream 20', 54' substantially includes one or more of methyl chloride, methylene chloride, chloroform, and carbon tetrachloride, which refers to a feed stream that does not include appreciable amounts of constituents other than methyl chloride, methylene chloride, chloroform, and carbon tetrachloride. In one or more embodiments, this stream consists essentially of one or more of methyl chloride, methylene chloride, chloroform, and carbon tetrachloride, which refers to a composition that is free of other constituents that would otherwise materially impact the basic and novel characteristics of embodiments of the invention. In one or more embodiments, this stream consists of one or more of methyl chloride, methylene chloride, chloroform, and carbon tetrachloride. In one or more embodiments, this stream includes from about 95.0 to about 100 wt. %, of methyl chloride, methylene chloride, chloroform, and carbon tetrachloride. In one or more embodiments, this stream includes from about 99.0 to about 100 wt. %, of methyl chloride, methylene chloride, chloroform, and carbon tetrachloride. In one or more embodiments, this stream includes from about 99.5 to about 100 wt. %, of methyl chloride, methylene chloride, chloroform, and carbon tetrachloride. In one or more embodiments, chloromethanes stream 20', 54' includes less than 7,000 ppm, in other embodiments less than 6,000 ppm, in other embodiments less than 5,500 ppm, in other embodiments less than 5,000 ppm, in other embodiments less than 2,500 ppm, and in other embodiments less than 1,000 ppm, of chlorinated organic constituents (e.g. ethylene dichloride, perchloroethylene) other than methyl chloride, methylene chloride, chloroform, and carbon tetrachloride.

In one or more embodiments, chloromethanes stream 20', 54' substantially includes one or more of methylene chloride, chloroform, and carbon tetrachloride, which refers to a feed stream that does not include appreciable amounts of constituents other than methylene chloride, chloroform, and carbon tetrachloride. In one or more embodiments, this stream consists essentially of one or more of methylene chloride, chloroform, and carbon tetrachloride, which refers to a composition that is free of other constituents that would otherwise materially impact the basic and novel characteristics of embodiments of the invention. In one or more embodiments, this stream consists of one or more of methylene chloride, chloroform, and carbon tetrachloride. In one or more embodiments, this stream includes from about 95.0 to about 100 wt. %, of methylene chloride, chloroform, and carbon tetrachloride. In one or more embodiments, this stream includes from about 99.0 to about 100 wt. %, of methylene chloride, chloroform, and carbon tetrachloride. In one or more embodiments, this stream includes from about 99.5 to about 100 wt. %, of methylene chloride, chloroform, and carbon tetrachloride. In one or more embodiments, chloromethanes stream 20', 54' includes less than 7,000 ppm, in other embodiments less than 6,000 ppm, in other embodiments less than 5,500 ppm, in other embodiments less than 5,000 ppm, in other embodiments less than 2,500 ppm, and in other embodiments less than 1,000 ppm, of chlorinated organic constituents (e.g. ethylene dichloride, perchloroethylene) other than methylene chloride, chloroform, and carbon tetrachloride.

In one or more embodiments, chloromethanes stream 20', 54' includes from about 40 wt. % to about 80 wt. % methylene chloride, from about 10 wt. % to about 45 wt. % chloroform, and from about 5 wt. % to about 20 wt. % carbon tetrachloride. In one or more embodiments, chloromethanes stream 20', 54' includes from about 50 wt. % to about 70 wt. % methylene chloride, from about 20 wt. % to about 40 wt. % chloroform, and from about 5 wt. % to about 15 wt. % carbon tetrachloride. In one or more embodiments, chloromethanes stream 20', 54' includes from about 55 wt. % to about 65 wt. % methylene chloride, from about 25 wt. % to about 35 wt. % chloroform, and from about 7 wt. % to about 13 wt. % carbon tetrachloride. In one or more embodiments, chloromethanes stream 20', 54' includes about 60 wt. % methylene chloride, about 30 wt. % chloroform, and about 10 wt. % carbon tetrachloride.

In one or more embodiments, chloromethanes stream 20', 54', which may be referred to as a chloroform feed stream 20', 54', is substantially chloroform, which refers to a feed stream that does not include appreciable amounts of constituents other than chloroform. In one or more embodiments, chloroform feed stream 20', 54' consists essentially of chloroform, which refers to a composition that is free of other constituents that would otherwise materially impact the basic and novel characteristics of embodiments of the invention. In one or more embodiments, chloroform feed stream 20', 62 consists of chloroform. In one or more embodiments, the chloroform is technical-grade chloroform. In other embodiments, fluorocarbon-grade chloroform is employed. In yet other embodiments, the chloroform may include a feed from other synthetic processes such as the production of chloromethanes. In one or more embodiments, chloroform feed stream 20', 54' includes from about 99.8 to about 100 wt. %, chloroform. In one or more embodiments, chloroform feed stream 20', 62 includes less than 5000 ppm, in other embodiments less than 2500 ppm, in other embodiments less than 2000 ppm, in other embodiments less than 1000 ppm, in other embodiments less than 750 ppm, and in other embodiments less than 500 ppm of constituents other than chloroform.

In one or more embodiments, chloromethanes stream 20', 54' may be devoid, or substantially devoid, of methane. In one or more embodiments, chloromethanes stream 20', 54' may include less than 1,000 ppm, in other embodiments less than 500 ppm, and in other embodiments less than 100 ppm methane. Embodiments where chloromethanes feed stream 20', 54' is devoid, or substantially devoid, of methane may allow utilization of lower pressures, and therefore less capital and energy costs may be incurred. In one or more embodiments, all feed streams to the process may be devoid, or substantially devoid, of methane.

In one or more embodiments, chloromethanes stream 20', 54' may be devoid, or substantially devoid, of methyl chloride. In one or more embodiments, chloromethanes stream 20', 54' may include less than 1,000 ppm, in other embodiments less than 500 ppm, and in other embodiments less than 100 ppm methyl chloride. In one or more embodiments, all feed streams to the process may be devoid, or substantially devoid, of methyl chloride.

Any carbon tetrachloride present in chloromethanes stream 20', 54' may be referred to as initial carbon tetrachloride inasmuch as a separate carbon tetrachloride feed stream may be provided.

Characteristics of Reaction Mixture

In one or more embodiments, the reaction mixture (e.g. reaction mixture 22 or the contents of reactor 53), which includes carbon tetrachloride, chlorine, hydrogen chloride, and chloroform (generally, chloromethanes), as well as residual byproducts such as heavy chlorinated organics, is maintained at a temperature and pressure that will maintain the carbon tetrachloride in the liquid state. As the skilled person will appreciate, a higher operating pressure will allow for a higher operating temperature since the processes of the invention are desirably conducted in the liquid phase.

In one or more embodiments, the reaction mixture (e.g. mixture 22 or the contents of reactor 53), during and optionally prior to the reaction or chlorination step (e.g. reaction step 21), is subjected to conditions suitable for reacting the chlorine with the partially-chlorinated chloromethanes.

In one or more embodiments, the reaction mixture (e.g. mixture 22 or the contents of reactor 53), during and optionally prior to the reaction or chlorination step (e.g. reaction step 21), is maintained at a temperature greater than 10° C., in other embodiments greater than 15° C., and in other embodiments greater than 20° C. In these or other embodiments, the reaction mixture is maintained, both prior to or during the reaction step, at a temperature less than 70° C., in other embodiments less than 60° C., and in other embodiments less than 50° C. In one or more embodiments, the reaction mixture is maintained, both prior to or during reaction step, at a temperature of from about 10 to about 70° C., in other embodiments from about 15 to about 60° C., or in other embodiments from about 20 to about 50° C. In one or more embodiments, the reaction mixture (e.g. mixture 22 or the contents of reactor 53) is maintained at a temperature and pressure sufficient to maintain relatively high levels of chlorine, as well as the chloroform, within the carbon tetrachloride medium.

In one or more embodiments, the reaction mixture (e.g. mixture 22 or the contents of reactor 53) is maintained, both prior to or during the reaction or chlorination step (e.g. step 21), under a pressure greater than 0.8, in other embodiments greater than 0.9, and in other embodiments greater than 0.95 atmospheres. In these or other embodiments, the reaction mixture is maintained, both prior to or during the reaction step, under a pressure less than 15, in other embodiments less than 10, and in other embodiments less than 5 atmospheres. In one or more embodiments, the reaction mixture is maintained, both prior to or during the reaction step, under a pressure from about 0.8 to about 15, in other embodiments from about 0.9 to about 10, or in other embodiments from about 0.95 to about 5 atmospheres.

In one or more embodiments, the reaction mixture (e.g. mixture 22 or the contents of reactor 53), during and optionally prior to the reaction or chlorination step (e.g. reaction step 21), is maintained at a temperature below the boiling point of the reaction mixture in the reactor at a given pressure. This may include avoiding boiling substantial amounts of lighter components overhead of the reactor.

In one or more embodiments, the reaction mixture (e.g. mixture 22 or the contents of reactor 53) is maintained, both prior to or during the reaction or chlorination step (e.g. step 21), under agitation. In one or more embodiments, the agitation is sufficient to achieve turbulent flow through the reactor in which the reaction takes place (e.g. reactor 53). In one or more embodiments, the agitation is sufficient to achieve turbulence that can be quantified by a Reynolds number of greater than 4000, in other embodiments greater than 10,000, and in other embodiments greater than 20,000. In one or more embodiments, the agitation is sufficient to achieve turbulence that can be quantified by a Reynolds number of greater than 100,000, in other embodiments greater than 200,000, in other embodiments greater than 400,000, and in other embodiments greater than 800,000. In these or other embodiments, the reaction mixture is maintained, both prior to or during the reaction step (e.g. step 21), is agitated to provide turbulence that can be quantified by a Reynolds number of from about 4000 to about 30,000, in other embodiments from about 8,000 to about 28,000, or in other embodiments from about 10,000 to about 26,000. In one or more embodiments, the photochlorination process of the present invention is conducted within a reactor (e.g. reactor 53) that is a well-mixed reactor with sufficient agitation to approach the ideal continuously-stirred tank reactor (CSTR). As mentioned elsewhere herein, in one or more embodiments, the reaction mixture (e.g. mixture 22 or the contents of reactor 53) is devoid of agitation by way of an agitator during the reaction or chlorination step (e.g. step 21). In these or other embodiments, some minimal amount, but a suitable amount to accomplish the desired reaction, of agitation may occur based simply on the introduction of the one or more feed streams and/or one or more recirculation streams and/or product formation in the form of gaseous products, such as HCl.

As suggested above, the introduction of chloromethanes (e.g. chloroform) to the reaction mixture (e.g. mixture 22 or the contents of reactor 53), which feed rate thereby regulates the concentration of chloromethanes within the reactor, is provided in an amount and in a manner that gives substantially instantaneous reaction of the partially-chlorinated chloromethanes to carbon tetrachloride in the presence of the UV light. It has been unexpectedly discovered that the dilution and dispersion of the partially-chlorinated chloromethanes, which is miscible in the carbon tetrachloride in the reactor, immediately prior to and during the reaction step (e.g. step 21) may be a critical parameter to obtaining the advantageous results of the invention.

In one or more embodiments, the feed rate of the chloromethanes to the reactor (e.g. reactor 53) can be quantified relative to the carbon tetrachloride within the reactor. In one or more embodiments, the feed rate of chloromethanes is greater than 10, in other embodiments greater than 15, in other embodiments greater than 25, in other embodiments greater than 35, in other embodiments greater than 45, in other embodiments greater than 55, in other embodiments greater than 65, in other embodiments greater than 75, in other embodiments greater than 85, in other embodiments greater than 95, in other embodiments greater than 110, and in other embodiments greater than 120 pounds per hour per 1000 pounds of carbon tetrachloride within the reactor. In these or other embodiments, the feed rate of chloromethanes is less than 1000, in other embodiments less than 800, in other embodiments less than 650, in other embodiments less than 500, in other embodiments less than 250, in other embodiments less than 200, in other embodiments less than 150, in other embodiments less than 125, in other embodiments less than 100, in other embodiments less than 80, in other embodiments less than 60, in other embodiments less than 40, in other embodiments less than 30, and in other embodiments less than 25 pounds per hour per 1000 pounds of carbon tetrachloride within the reactor. In one or more embodiments, the feed rate of the chloromethanes is from about 10 to about 1000, in other embodiments from about 25 from about 650, and in other embodiments from about 55 to about 200 pounds per hour per 1000 pounds of carbon tetrachloride within the reactor.

In one or more embodiments, the dilution of the chloromethanes feed can also be quantified based upon the amount of partially-chlorinated chloromethanes within the reaction mixture (e.g. mixture 22 or the contents of reactor 53). For example, the concentration of partially-chlorinated chloromethanes within the reaction mixture can be quantified based upon the weight of partially-chlorinated chloromethanes relative to the weight of the reaction mixture, which reaction mixture includes the carbon tetrachloride, chlorine, hydrogen chloride, and partially-chlorinated chloromethanes. As a skilled person will appreciate, these amounts (i.e. the partially-chlorinated chloromethanes within the reaction mixture) can be determined by measuring the amount of partially-chlorinated chloromethanes within the reactor effluent (i.e. at the outlet), which in a well-stirred reactor is equivalent to the amount of partially-chlorinated chloromethanes at the reaction zone, where the reaction zone refers to that location within the reaction medium (i.e. within the reactor) in which chlorination of the chloromethanes takes place (i.e. the reaction mixture is subjected to the appropriate wavelength of electromagnetic radiation). In one or more embodiments, the concentration of partially-chlorinated chloromethanes within the reaction mixture is less than 5 wt. % (50,000 ppm), in other embodiments less than 4 wt. %, in other embodiments less than 3 wt. %, in other embodiments less than 2 wt. %, and in other embodiments less than 1 wt. % partially-chlorinated chloromethanes based upon the total weight of the reaction mixture. In one or more embodiments, the concentration of partially-chlorinated chloromethanes within the reaction mixture is less than 5,000 ppm (by weight), in other embodiments less than 4,000 ppm, in other embodiments less than 3,000 ppm, and in other embodiments less than 2,000 ppm chloromethanes based upon the total weight of the reaction mixture. In one or more embodiments, the concentration of partially-chlorinated chloromethanes within the reaction mixture is less than 1,000 ppm (by weight), in other embodiments less than 750 ppm, in other embodiments less than 500 ppm, and in other embodiments less than 200 ppm partially-chlorinated chloromethanes based upon the total weight of the reaction mixture. In one or more embodiments, the concentration of partially-chlorinated chloromethanes within the reaction mixture is from about 1 to about 5,000 ppm, in other embodiments from about 50 to about 3,000 ppm, and in other embodiments from about 100 to about 2,000 ppm partially-chlorinated chloromethanes based upon the entire weight of the reaction mixture. In one or more embodiments, the concentration of partially-chlorinated chloromethanes within the reaction mixture is from about 1 to about 50,000 ppm, in other embodiments from about 50 to about 30,000 ppm, and in other embodiments from about 100 to about 20,000 ppm partially-chlorinated chloromethanes based upon the entire weight of the reaction mixture. In one or more embodiments, the concentration of partially-chlorinated chloromethanes within the reaction mixture is from about 1 to about 1,000 ppm, in other embodiments from about 50 to about 750 ppm, and in other embodiments from about 100 to about 500 ppm chloromethanes based upon the entire weight of the reaction mixture.

As suggested above, the amount of chlorine present during the reaction step (e.g. reaction step 21) or, stated another way, within the reaction mixture, is believed to be an important parameter for practicing the invention. In one or more embodiments, the introduction of chlorine to the reaction mixture (e.g. to vessel 53) is provided in an amount and in a manner that provides the reaction with at least a stoichiometric amount, or a stoichiometric excess of, chlorine, relative to the partially-chlorinated chloromethanes. In one or more embodiments, the concentration of the chlorine within the reaction medium (i.e. carbon tetrachloride) is at the saturation level for chlorine within the carbon tetrachloride at the temperature and pressure at which the reaction is performed. In one or more embodiments, the amount of chlorine with the reactor (e.g. reactor 53) is sufficient to maintain appreciable levels of chlorine within the head space of the reactor. To the extent that excess chlorine is fed to the reactor relative to the partially-chlorinated chloromethanes, the concentration of chlorine within the reactor can continue to build over time until a saturation level is achieved relative to the temperature and pressure within the reactor, although recirculation of the carbon tetrachloride through a recirculation loop may serve to modulate the amount of chlorine within the reactor.

For example, where the chloromethanes stream is substantially chloroform, the amount of chlorine introduced to the reaction mixture can be quantified based upon the molar ratio of chlorine to chloroform fed to the reactor. In one or more embodiments, the molar ratio of chlorine to chloroform that is fed to, for example, reactor 53, is greater than 1.00:1.00, in other embodiments greater than 1.02:1.00, and in other embodiments greater than 1.04:1.00. In one or more embodiments, the molar ratio of chlorine to chloroform is from about 1.00:1.00 to about 1.10:1.00, in other embodiments from about 1.01:1.00 to about 1.08:1.00, in other embodiments from about 1.02:1.00 to about 1.06:1.00, in other embodiments, from about 1.00:1.00 to about 1.50: 1.00, in other embodiments from about 1.02:1.00 to about 1.40:1.00, and in other embodiments from about 1.06:1.00 to about 1.30:1.00.

One skilled in the art should recognize that the above ratios are based on chloroform and the required stoichiometric amounts are based thereon (i.e. one chlorine atom or radical reacts with one chloroform molecule). To the extent other partially-chlorinated methanes are in the reaction mixture, the amount of chlorine required to convert those partially-chlorinated methanes to carbon tetrachloride should be adjusted to maintain similar excesses of chlorine.

In one or more embodiments, the amount of chlorine introduced to the reaction mixture can be quantified based upon a molar excess % of chlorine to all partially-chlorinated methanes fed to the reactor. Stated differently, the excess of chlorine is calculated relative to the stoichiometric requirement of any given partially-chlorinated methanes in order to achieve carbon tetrachloride from the partially-chlorinated methanes. In one or more embodiments, the amount of chlorine may be at a molar excess of at least 2%, in other embodiments, at least 5%, in other embodiments, at least 10%, in other embodiments, at least 15%, and in other embodiments, at least 20%, for all partially-chlorinated methanes fed to the reactor. In these or other embodiments, the amount of chlorine may be at a molar excess of less than 50%, in other embodiments, less than 40%, in other embodiments, less than 30%, and in other embodiments, less than 25%, for all partially-chlorinated methanes fed to the reactor. These end points, and any other end points provided herein, may be utilized to form any suitable ranges.

It should be appreciated by the skilled person that the amount of chlorine required or provided may be pressure dependent. That is, at relatively lower pressures, relatively higher amounts of chlorine may be required or provided due to lower solubility of chlorine. Similarly, at relatively higher pressures, relatively lower amounts of chlorine may be required or provided due to higher solubility of chlorine.

It should be appreciated by the skilled person that the amount of chlorine required or provided may be even higher than those amounts disclosed herein, though this will generally require additional operational and/or manufacturing costs, such as in the form larger equipment in order to recycle the excess chlorine. In some embodiments, this even further excess chlorine and the associated additional operational and/or manufacturing costs may be desirable.

In these or other embodiments, the amount of chlorine employed in the process of the present invention can be quantified based upon the concentration of chlorine within the reaction mixture. As a skilled person will appreciate, these amounts (i.e. the chlorine within the reaction mixture) can be determined by measuring the amount of chlorine within the reactor effluent (i.e. at the outlet), which in a well-stirred reactor is equivalent to the amount of chlorine at the reaction zone, where the reaction zone refers to that location within the reaction medium (i.e. within the reactor) in which chlorination of the chloroform takes place. In one or more embodiments, the concentration of chlorine within the effluent is greater than 0.01 wt. %, in other embodiments greater than 0.1 wt. %, in other embodiments greater than 0.3 wt. %, in other embodiments greater than 0.6 wt. %, in other embodiments greater than 1.2 wt. %, in other embodiments greater than 1.5 wt. %, in other embodiments greater than 1.8 wt. %, and in other embodiments greater than 2.0 wt. % based upon the total weight of the reaction mixture. In these or other embodiments, the concentration of chlorine within the reactor effluent is at saturation level for the given temperature and pressure, in other embodiments less than 5 wt. %, in other embodiments less than 4.6 wt. %, and in other embodiments less than 4.2 wt. % based upon the total weight of the reaction mixture. In one or more embodiments, the concentration of chlorine within the reactor effluent is from about 0.01 wt. % to saturation, in other embodiments from about 0.1 to about 5 wt. %, in other embodiments from about 0.3 to about 5 wt. %, in other embodiments from about 1.8 to about 4.6 wt. %, and in other embodiments from about 2.0 wt % to about 4.2 wt % based upon the total weight of the reaction mixture. It should also be appreciated that the above provided molar ratios of chlorine to chloroform, and the above provided concentrations of chloroform within the reaction mixture, may be utilized to form other suitable concentrations of chlorine by using the respective molecular weights and corresponding conversions.

In one or more embodiments, the reaction mixture includes less than 0.5 ppm, in other embodiments less than 0.3 ppm, in other embodiments less than 0.2 ppm, in other embodiments less than 0.15 ppm, and in other embodiments less than 0.1 ppm of iron. It is generally believed that lower amounts of iron, particularly embodiments below 0.3 ppm in the reaction mixture, may prevent significant scale from forming on the lamp well.

In one or more embodiments, the reactor (e.g. reactor 53) avoids the use of materials that are corrosive with respect to the reaction mixture. In one or more embodiments, the reactor avoids the use of iron-based materials. In one or more embodiments, the reactor avoids the use of stainless steel materials. In one or more embodiments, the reactor and/or certain components thereof (e.g. agitation element 65) are made from a nickel-copper based alloys, such as Monel™ 400 and Monel™ K500. Other materials that are suitable for the reactor and/or components of the reactor include polyethylene, polytetrafluoroethene, glass, and tantalum.

Characteristics of Electromagnetic Radiation

In one or more embodiments, the electromagnetic radiation employed in practicing the present invention (e.g. generated by lamp 63) is characterized by including a wavelength of from about 200 to about 500 nm, in other embodiments from about 200 to about 400 nm, in other embodiment from about 280 to about 380 nm, in other embodiments from about 300 to about 350 nm, in other embodiments from about 330 to about 530 nm, and in other embodiments from about 360 to about 500 nm. In these or other embodiments, the electromagnetic radiation is characterized by a wavelength distribution, based upon relative intensity, where from about 50 to about 60% of the electromagnetic radiation has a wavelength of about 280 to about 435 nm, in these or other embodiments where from about 40 to about 50% of the electromagnetic radiation has a wavelength of about 300 to about 380 nm, and in these or other embodiments where from about 20 to about 30% of the electromagnetic radiation has a wavelength of about 330 to about 370 nm. In one or more embodiments, the electromagnetic radiation includes ultraviolet light.

In one or more embodiments, the electromagnetic radiation employed in practicing the present invention (e.g. generated by lamp 63) is characterized by including a wavelength of from about 470 to about 530 nm, in other embodiments from about 480 to about 510 nm, in other embodiment from about 490 to about 500 nm, and in other embodiments 495 nm or approximate thereto. In one or more embodiments, the electromagnetic radiation is characterized by a wavelength distribution, based upon relative intensity, where at least 50%, and in other embodiments, at least 80% of the electromagnetic radiation has a wavelength of 495 nm or approximate thereto.

In one or more embodiments, the electromagnetic radiation employed in practicing the present invention (e.g. generated by lamp 63) is characterized by including a wavelength of from about 350 to about 420 nm, in other embodiments from about 370 to about 400 nm, in other embodiments from about 380 to about 390 nm, and in other embodiments 385 nm or approximate thereto. In one or more embodiments, the electromagnetic radiation is characterized by a wavelength distribution, based upon relative intensity, where at least 50%, and in other embodiments, at least 80% of the electromagnetic radiation has a wavelength of 385 nm or approximate thereto.

In one or more embodiments, the electromagnetic radiation employed in practicing the present invention (e.g. generated by lamp 63) is characterized by including a wavelength of from about 330 to about 400 nm, in other embodiments from about 350 to about 380 nm, in other embodiments from about 360 to about 370 nm, and in other embodiments 365 nm or approximate thereto. In one or more embodiments, the electromagnetic radiation is characterized by a wavelength distribution, based upon relative intensity, where at least 50%, and in other embodiments, at least 80% of the electromagnetic radiation has a wavelength of 365 nm or approximate thereto.

In one or more embodiments, the electromagnetic radiation employed in practicing the present invention (e.g. generated by lamp 63) is characterized as including a wavelength distribution that avoids the formation of ozone. As the skilled person appreciates, this may be defined by the theoretical wavelength needed to activate oxygen, which in some embodiments is 240 nm or approximate thereto. In one or more embodiments, the electromagnetic radiation is devoid of wavelengths shorter than 230 nm, in other embodiments shorter than 240 nm, in other embodiments shorter than 250 nm, and in other embodiments shorter than 260 nm.

In one or more embodiments, employing the electromagnetic radiation at a wavelength distribution that avoids the formation of ozone allows for advantageous oxygenate-containing mediums, such as air, to be used as a cooling medium for the lamp. In other embodiments, oxygenate-free mediums, such as nitrogen and water, to be used as a cooling medium for the lamp.

In one or more embodiments, the electromagnetic radiation employed in practicing the present invention (e.g. generated by lamp 63) is characterized by a wavelength spanning a band of about 30 nm, in other embodiments about 20 nm, in other embodiment about 15 nm, and in other embodiments about 10 nm.

In one or more embodiments, the electromagnetic radiation is provided from one or more light producing lamps that operate at 40 to about 20,000, in other embodiments from about 75 to about 18,000, an in other embodiments from about 100 to about 10,000 W. In one or more embodiments, the electromagnetic radiation is provided from one or more mercury lamps. In one or more embodiments, the electromagnetic radiation is provided from one or more light-emitting diodes.

Characteristics of Product Stream

As discussed above, the carbon tetrachloride crude product stream (e.g. streams 28' and 66') includes the desired carbon tetrachloride product, chlorine, and hydrogen chloride as well as residual byproducts such as heavy chlorinated organics. In one or more embodiments, these product streams (e.g. 28', 66') are substantially carbon tetrachloride, chloroform, hydrogen chloride, and optionally chlorine, which refers to a product stream that does not include appreciable amounts of constituents other than carbon tetrachloride, chloroform, hydrogen chloride, and optionally chlorine. In one or more embodiments, the product stream (e.g. 28', 66') consists essentially of carbon tetrachloride, optionally chloroform, optionally hydrogen chloride, and optionally chlorine, which refers to a composition that is free of other constituents that would otherwise materially impact the basic and novel characteristics of embodiments of the invention. In one or more embodiments, the product stream (e.g. 28', 66') consists of carbon tetrachloride, optionally chloroform, optionally hydrogen chloride, and optionally chlorine.

In one or more embodiments, the product stream (e.g. 28', 66') includes less than 2500 ppm, in other embodiments less than 1000 ppm, in other embodiments less than 500 ppm, in other embodiments less than 250 ppm, and in other embodiments less than 100 ppm (parts per million by weight) chlorinated hydrocarbons other than carbon tetrachloride (e.g. hexachloroethane).

In one or more embodiments, the product stream (e.g. 28', 66') includes less than 2500 ppm, in other embodiments less than 1000 ppm, in other embodiments less than 750 ppm, and in other embodiments less than 500 ppm (parts per million by weight) of constituents other than carbon tetrachloride, hydrogen chloride, and chlorine.

In one or more embodiments, the product stream (e.g. 28', 66') is characterized by an advantageously low level of chloroform, which is indicative of high reaction yield. In one or more embodiments, the reaction yield, relative to chloroform, is greater than 90.00%, in other embodiments greater than 92.00%, in other embodiments greater than 95.00%, in other embodiments greater than 97.00%, in other embodiments greater than 98.00%, in other embodiments greater than 99.00%, in other embodiments greater than 99.50%, and in other embodiments greater than 99.99%. In particular embodiments, the yield, relative to chloroform, is 100%. As a result, product stream 28', 66' may include less than 6000 ppm, in other embodiments less than 5500 ppm, in other embodiments less than 5000 ppm, in other embodiments less than 4500 ppm, in other embodiments less than 4000 ppm, in other embodiments less than 3000 ppm, in other embodiments less than 2000 ppm, in other embodiments less than 1000 ppm, in other embodiments less than 500 ppm, in other embodiments less than 250, in other embodiments less than 100, in other embodiments less than 50, and in other embodiments less than 10 ppm (parts per million by weight) chloroform.

Reaction Mechanism

As suggested herein, the manner and sequence of this process is believed to encourage the formation chlorine free radicals and reaction of these radicals with chloroform prior to any side reactions (e.g. the dimerization of chloroform) to thereby increase the selectivity of the reaction. Without wishing to be bound by any particular theory, it is believed that the following reactions take place during one or more steps of the present invention:

$Cl_2 + h\nu \rightarrow 2Cl^*$                       (1) Initiation

$CHCl_3 + Cl^* \rightarrow CCl_3^* + HCl$         (2) Propagation

$CCl_3^* + Cl_2 \rightarrow CCl_4 + Cl^*$            (3) Propagation $CCl_3^* + CCl_3^* \rightarrow C_2Cl_6$               (4) Termination $CCl_3^* + Cl^* \rightarrow CCl_4$                 (5) Termination $Cl^* + Cl^* \rightarrow Cl_2$                     (6) Termination.

Reactions 1-3 are the desired pathway to convert chloroform and chlorine gas into carbon tetrachloride and HCl byproduct. Reaction 5 leads to the desired product, but at the cost of terminating the free radical reaction chain. Reaction 4 terminates the chain and includes the formation of hexachloroethane by the dimerization of two trichloromethyl radicals; this reaction is substantially avoided by the present invention. Reaction 6 terminates the reaction chain but provides chlorine that can again generate free radicals in the presence of an initiator, such as UV light.

INDUSTRIAL APPLICABILITY

In one or more embodiments, the crude product stream (e.g. streams 28' or 66', 73') from the photochlorination step or process, may be used in the synthesis of chlorinated organic compounds. As indicated above, the process of one or more embodiments of the present invention advantageously provides a product stream that can be directly used in these downstream synthetic processes without the need for separation steps, such as distillation steps, to remove heavier chlorinated organic byproducts such as hexachloroethane.

As discussed elsewhere herein, in one or more embodiments, the carbon tetrachloride produced according to embodiments of the invention, as a crude product stream, can be directly combined with an olefin and reacted in the presence of an appropriate catalyst to form a chlorinated propane and/or chlorinated propene. In this respect, U.S. Pat. Nos. 6,187,978 and 6,313,360; and U.S. Publication Nos. 2019/0284118; 2012/0310020; 2009/0216055; and 2004/0225166 are hereby incorporated by reference. This reaction may be referred to as a Kharasch reaction. In one or more embodiments, the crude carbon tetrachloride product stream may be subjected to purification processes to remove hydrogen chloride and/or chorine. In one or more embodiments, the crude carbon tetrachloride product stream does not require separation or purification from chlorinated organics before being combined with an olefin.

As further description of embodiments that include combining the crude carbon tetrachloride product stream with an olefin, exemplary olefins for use in these reactions include ethylene and vinyl chloride. The skilled person will appreciate that other olefins can likewise be used. The reaction between carbon tetrachloride and an olefin can be catalyzed by using a variety of catalytic species, many of which are or derive from species that are insoluble or only partially soluble in the reaction medium. A common catalyst or catalyst precursor is iron. The skilled person will appreciate that embodiments of the invention can likewise be extended to other insoluble or partially soluble catalysts or catalyst precursors. Additionally, the skilled person appreciates that these insoluble or partially soluble catalysts may be used in conjunction with an additional constituent, which may be referred to as cocatalysts, ligands, or chelating agents, which are believed to complement the catalyst. For example, tributylphosphate has been used in conjunction with an iron catalyst. The skilled person will appreciate that the invention can be extended to the use of other cocatalysts, ligands, or chelating agents.

In addition to embodiments where the crude product stream from the photochlorination step or process may be used in the synthesis of chlorinated organic compounds, in one or more embodiments, the photochlorination step or process may advantageously receive a crude product stream from a chloromethane step or process. In one or more embodiments, the chloromethanes reactant stream (i.e. 20', 54') includes a crude product stream from a chloromethanes production process after the production stream has optionally undergone separation (e.g. a distillation) to separate the chloromethanes from heavier compounds and to separate the chloromethanes from lighter inorganics such as hydrogen chloride. Advantageously, this crude product stream from a chloromethanes production process may be directly fed to the photochlorination step or process without the need to separate the various chloromethane constituents (i.e. chloroform need not be separated from methylene chloride).

Figure 4:
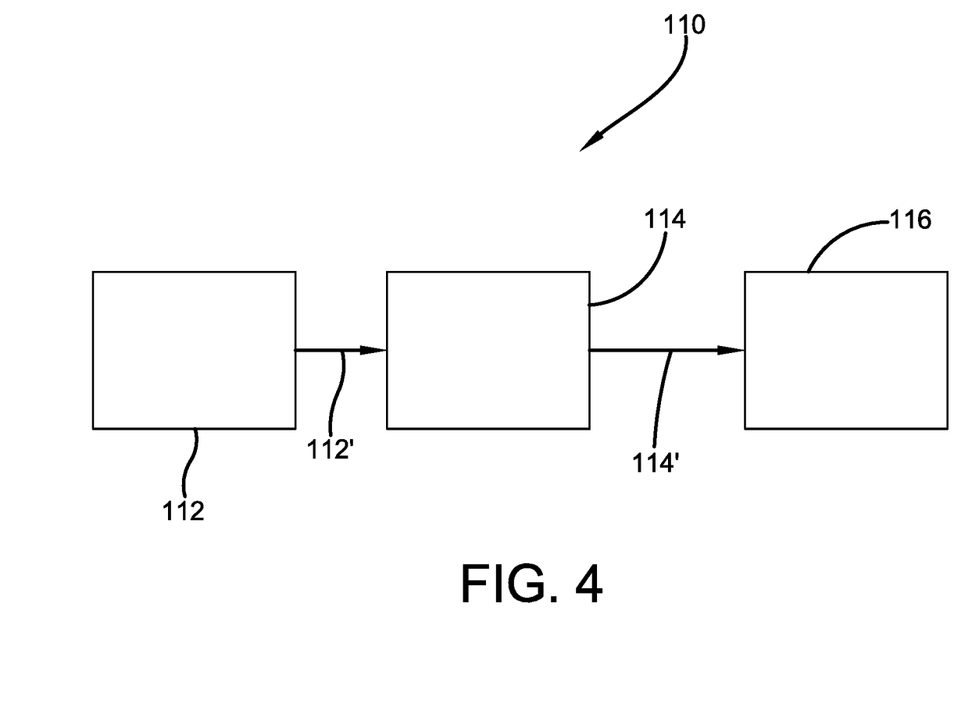
FIG. 4 is a flow chart representation of a process according to one or more embodiments of the present invention.

Embodiments where the photochlorination step or process receives a crude product stream from a chloromethane step or process and/or where a crude product stream from the photochlorination step or process may be used in the subsequent synthesis of chlorinated organic compounds may be referred to as an integrated process. With particular reference to FIG. 4, aspects of the invention include an integrated process 110 that includes a chloromethanes process 112, which may also be referred to as a chloromethanes step 112, integrated with a photochlorination process 114, which may also be referred to as a photochlorination step 114, that is integrated with a chlorinated organics synthetic process 116, which may also be referred to as a chlorinated organics synthetic step 116.

In one or more embodiments, chloromethanes process 112 may include the type where a chlorine-containing feed stream and an organic-compound containing feed stream are fed to a reactor. A product stream 112' from chloromethanes process 112 (e.g. chloromethanes stream 20', 54') may be provided to a photochlorination process 114. Photochlorination process 114 can include those processes or systems described elsewhere herein. That is, stream 112' from chloromethanes process 112 may be provided as, or as a portion of, chloromethanes stream 20', 54' for a photochlorination process or system described herein.

In one or more embodiments, process 112 may be of the type where the organic-compound containing feed stream includes only, or substantially only, methanol. These embodiments generally utilize a two-step reaction in chloromethanes process 112. In the first step, the methanol is reacted under suitable reaction conditions to form methyl chloride, such as in a hydrochlorination reaction with hydrogen chloride. Then, the second step includes reacting the methyl chloride with chlorine under suitable reaction conditions, such as by thermal chlorination, to form methylene chloride, chloroform, and carbon tetrachloride.

In other embodiments, process 112 may be of the type where the organic-compound containing feed stream includes only, or substantially only, methane. These embodiments generally utilize a one-step reaction in chloromethanes process 112, where the methane is reacted with chlorine under suitable reaction conditions to form methyl chloride, methylene chloride, chloroform, and carbon tetrachloride.

In one or more embodiments, stream 112' may include a product stream that has undergone separation (e.g. distillation) before being provided to form a photochlorination process 114. This separation step may include separating carbon tetrachloride and lighter components (e.g. partially-chlorinated chloromethanes) from components that are heavier than carbon tetrachloride. Additionally, this separation step may include separating hydrogen chloride from the carbon tetrachloride and partially-chlorinated chloromethanes to provide chloromethanes stream, which may be provided to photochlorination process 114. The hydrogen chloride stream may be further utilized in a separate process.

A product stream 114' from photochlorination process 114 may be provided to a subsequent synthetic process 116, as further described above. In one or more embodiments, stream 114' may be directly fed to an olefin addition process. For example, the carbon tetrachloride in crude stream 114' may be combined with an olefin, such as ethylene or vinyl chloride, for the manufacture of chlorinated propanes. Subsequent synthetic process 116 may include any suitable processes, such as those that involve an appropriate catalyst to form chlorinated alkanes or alkenes using various synthetic techniques such as the Kharasch reaction. An olefin-containing stream (not shown) may be provided to subsequent synthetic process 116.

In one or more embodiments, stream 114' may be stripped of chlorine before being provided to subsequent synthetic process 116. Advantageously, in one or more embodiments, stream 114' need not undergo other separations (e.g. distillations) to remove, for example, organic compounds, from stream 114', which substantially includes carbon tetrachloride prior to introducing stream 114' to the subsequent synthetic process 116. As suggested above, steam 114' advantageously includes less than appreciable amounts of unreacted partially-chlorinated chloromethanes and/or heavier organic components.

In one or more embodiments, chloromethanes process 112, photochlorination process 114, and subsequent synthetic process 116 may be located at the same chemical facility. In one or more embodiments, chloromethanes process 112, photochlorination process 114, and subsequent synthetic process 116 may be operated continuously. In one or more embodiments, chloromethanes process 112, photochlorination process 114, and subsequent synthetic process 116 may be within 20 miles, in other embodiments within 10 miles, in other embodiments within 5 miles, in other embodiments within 1 mile, and in other embodiments within 0.5 miles of each other. In one or more embodiments, chloromethanes process 112, photochlorination process 114, and subsequent synthetic process 116 are coupled by fixed pipelines. This may be referred to as chloromethanes process 112 occurring in a first vessel, photochlorination process 114 occurring in a second vessel, and subsequent synthetic process 116 occurring in a third vessel, and the first vessel, the second vessel, and the third vessel being coupled by fixed pipelines.

Specific Embodiments

The following embodiments are provided in accordance with the present disclosure.

Paragraph A: A method including providing a chloromethanes stream including chloroform, initial carbon tetrachloride, and at least one of methyl chloride and methylene chloride; combining the chloromethanes stream with chlorine and additional carbon tetrachloride to form a reaction mixture, wherein the reaction mixture includes at least stoichiometric levels of chlorine relative to the chloroform and the at least one of methyl chloride and methylene chloride; introducing electromagnetic radiation to the reaction mixture and subjecting the reaction mixture to conditions suitable for reacting the chlorine with the chloroform and the at least one of methyl chloride and methylene chloride to thereby form product carbon tetrachloride; and collecting a product stream after the step of introducing.

Paragraph B: The method of paragraph A, wherein the chloromethanes stream includes from about 99.0 to about 100 wt. %, of the chloroform, the initial carbon tetrachloride, and the at least one of methyl chloride and methylene chloride.

Paragraph C: The method of either of paragraph A or paragraph B, wherein the product stream includes less than 2,500 ppm (parts per million by weight) of chlorinated hydrocarbons other than carbon tetrachloride.

Paragraph D: The method of any of paragraph A through paragraph C, wherein the concentration of the chloroform and the at least one of methyl chloride and methylene chloride in the reaction mixture is less than 50,000 ppm by weight relative to the weight of the reaction mixture.

Paragraph E: The method of any of paragraph A through paragraph D, further comprising a step of combining the product stream with an olefin, a catalyst, and a chelating agent to thereby react the carbon tetrachloride in the product stream with the olefin.

Paragraph F: The method of any of paragraph A through paragraph E, wherein the olefin includes ethylene or vinyl chloride, wherein the catalyst includes iron, and wherein the chelating agent includes tributylphosphate.

Paragraph G: The method of any of paragraph A through paragraph F, wherein the chloromethanes stream includes the methylene chloride.

Paragraph H: The method of any of paragraph A through paragraph G, further comprising a step of combining methanol with hydrogen chloride under suitable reaction conditions to thereby form initial methyl chloride.

Paragraph I: The method of any of paragraph A through paragraph H, further comprising a step of combining the initial methyl chloride with chlorine under suitable reaction conditions to thereby form the methylene chloride, the chloroform, and the initial carbon tetrachloride.

Paragraph J: The method of any of paragraph A through paragraph I, wherein the chloromethanes stream includes both the methyl chloride and the methylene chloride.

Paragraph K: The method of any of paragraph A through paragraph J, further comprising a step of combining methane with chlorine under suitable reaction conditions to thereby form the methyl chloride, the methylene chloride, the chloroform, and the initial carbon tetrachloride.

Paragraph L: The method of any of paragraph A through paragraph K, wherein the electromagnetic radiation has a wavelength spanning a band of about 30 nm.

Paragraph M: The method of any of paragraph A through paragraph L, wherein the electromagnetic radiation is provided by a light-emitting diode.

Paragraph N: The method of any of paragraph A through paragraph M, further comprising a step of filtering iron from the chlorine.

Paragraph O: The method of any of paragraph A through paragraph N, wherein the chloromethanes stream is provided from a first vessel, wherein the steps combining the chloromethanes stream with chlorine and introducing electromagnetic radiation occur within a second vessel, and wherein the step combining the product stream with an olefin occurs within a third vessel.

Paragraph P: The method of any of paragraph A through paragraph O, wherein the first vessel, the second vessel, and the third vessel are coupled by fixed pipelines.

Paragraph Q: The method of any of paragraph A through paragraph P, wherein the step of combining the chloromethanes stream with chlorine includes providing the chlorine at a molar excess of from at least 5% to less than 40% with respect to the total of the chloroform and the at least one of methyl chloride and methylene chloride.

Paragraph R: The method of any of paragraph A through paragraph Q, wherein the product stream includes less than 1000 ppm hexachloroethane.

Paragraph S: The method of any of paragraph A through paragraph R, wherein the step of combining the chloromethanes stream with chlorine consumes greater than 99.00% of the chloroform.

Paragraph T: The method of any of paragraph A through paragraph S, wherein the method is devoid of a step of removing organic compounds from the product stream prior to the step of combining the product stream with an olefin.

Paragraph U: The method of any of paragraph A through paragraph T, wherein the chloromethanes stream includes from about 99.5 to about 100 wt. %, of the methyl chloride, the methylene chloride, the chloroform, and the initial carbon tetrachloride.

Paragraph V: The method of any of paragraph A through paragraph U, wherein the method is devoid of a step of separating chloromethanes before the step of combining the chloromethanes stream with chlorine.

Paragraph W: The method of any of paragraph A through paragraph V, wherein the product stream includes chlorine and hydrochloric acid, the method further comprising a step of scrubbing, with an additional amount of the chloromethanes stream, the chlorine and hydrochloric acid from the product stream.

Paragraph X: The method of any of paragraph A through paragraph W, wherein the step of combining the chloromethanes stream with chlorine includes introducing chlorine to the reactor at from 10% molar excess to 30% molar excess with respect to the total of the chloroform and the at least one of methyl chloride and methylene chloride within the reaction mixture.

Paragraph Y: The method of any of paragraph A through paragraph X, wherein the method is devoid of a step of agitating the reaction mixture with a mechanical agitator.

Paragraph Z: The method of any of paragraph A through paragraph Y, wherein a chlorine feed stream includes less than 1000 ppm of constituents other than chlorine.

Paragraph AA: The method of any of paragraph A through paragraph Z, wherein a reactor and/or certain components thereof (e.g. an agitation element) are made from a nickel-copper based alloy and/o avoid the use of iron-based materials and stainless steel materials.

Paragraph AB: The method of any of paragraph A through paragraph AA, wherein a reactor and/or certain components thereof (e.g. an agitation element) avoid the use of iron-based materials.

Paragraph AC: The method of any of paragraph A through paragraph AB, wherein a reactor and/or certain components thereof (e.g. an agitation element) avoid the use of stainless steel materials.

Various modifications and alterations that do not depart from the scope and spirit of this invention will become apparent to those skilled in the art. This invention is not to be duly limited to the illustrative embodiments set forth herein.

What is claimed is:

1. A method of producing carbon tetrachloride, the method comprising steps of:
   (i) providing a chloromethanes stream including chloroform, initial carbon tetrachloride, and at least one of methyl chloride and methylene chloride, wherein the chloromethanes stream includes from about 99.0 to about 100 wt. %, of the chloroform, the initial carbon tetrachloride, and the at least one of methyl chloride and methylene chloride;

(ii) combining the chloromethanes stream with chlorine and additional carbon tetrachloride to form a reaction mixture, wherein the reaction mixture includes at least stoichiometric levels of chlorine relative to the chloroform and the at least one of methyl chloride and methylene chloride;

(iii) introducing electromagnetic radiation to the reaction mixture and subjecting the reaction mixture to conditions suitable for reacting the chlorine with the chloroform and the at least one of methyl chloride and methylene chloride to thereby form product carbon tetrachloride; and (iv) collecting a product stream after step (iii), wherein the product stream includes less than 2,500 ppm (parts per million by weight) of chlorinated hydrocarbons other than carbon tetrachloride.

2. The method of claim 1, wherein the concentration of the chloroform and the at least one of methyl chloride and methylene chloride in the reaction mixture is less than 50,000 ppm by weight relative to the weight of the reaction mixture.

3. The method of claim 1, further comprising a step of:
(v) combining the product stream with an olefin, a catalyst, and a chelating agent to thereby react the carbon tetrachloride in the product stream with the olefin.

4. The method of claim 3, wherein the olefin includes ethylene or vinyl chloride, wherein the catalyst includes iron, and wherein the chelating agent includes tributylphosphate.

5. The method of claim 1, wherein the chloromethanes stream includes the methylene chloride, the method further comprising steps of:
(i-a) combining methanol with hydrogen chloride under suitable reaction conditions to thereby form initial methyl chloride; and
(i-b) combining the initial methyl chloride with chlorine under suitable reaction conditions to thereby form the methylene chloride, the chloroform, and the initial carbon tetrachloride.

6. The method of claim 1, wherein the chloromethanes stream includes both the methyl chloride and the methylene chloride, the method further comprising a step of:
(i-a) combining methane with chlorine under suitable reaction conditions to thereby form the methyl chloride, the methylene chloride, the chloroform, and the initial carbon tetrachloride.

7. The method of claim 1, wherein the electromagnetic radiation has a wavelength spanning a band of about 30 nm, and wherein the electromagnetic radiation is provided by a light-emitting diode, the method further comprising a step of:
(i-c) filtering iron from the chlorine prior to the step (ii).

8. The method of claim 3, wherein the step (i) is provided from a first vessel, wherein the steps (ii) and (iii) occur within a second vessel, and wherein the step (v) occurs within a third vessel, wherein the first vessel, the second vessel, and the third vessel are coupled by fixed pipelines.

9. The method of claim 1, wherein the step of combining the chloromethanes stream with chlorine includes providing the chlorine at a molar excess of from at least 5% to less than 40% with respect to the total of the chloroform and the at least one of methyl chloride and methylene chloride, wherein the product stream includes less than 1000 ppm hexachloroethane, and wherein the step (iii) consumes greater than 99.00% of the chloroform.

10. The method of claim 3, wherein the method is devoid of a step of removing organic compounds from the product stream between steps (iv) and (v).

11. The method of claim 1, wherein the chloromethanes stream further includes both the methyl chloride and the methylene chloride, and wherein the chloromethanes stream includes from about 99.5 to about 100 wt. %, of the methyl chloride, the methylene chloride, the chloroform, and the initial carbon tetrachloride.

12. The method of claim 5, wherein the method is devoid of a step of separating chloromethanes after step (i-a) and before step (ii).

13. The method of claim 3, wherein the product stream includes chlorine and hydrochloric acid, the method further comprising a step of:
(vi) scrubbing, with an additional amount of the chloromethanes stream, the chlorine and hydrochloric acid from the product stream.

14. The method of claim 1, wherein the step of combining the chloromethanes stream with chlorine includes introducing the chlorine to the reactor at from 10% molar excess to 30% molar excess with respect to the total of the chloroform and the at least one of methyl chloride and methylene chloride within the reaction mixture.

15. The method of claim 1, wherein the method is devoid of a step of agitating the reaction mixture with a mechanical agitator.

* * * * *